(12) United States Patent
Bi

(10) Patent No.: US 6,938,464 B1
(45) Date of Patent: Sep. 6, 2005

(54) DIGITAL VISCOMETER WITH FRICTIONLESS BEARING

(75) Inventor: Hongfeng Bi, 888 W Sam Houston Pkwy. S., Suite 125, Houston, TX (US) 77042

(73) Assignee: Hongfeng Bi, Houston, TX (US)

( * ) Notice: Subject to any disclaimer, the term of this patent is extended or adjusted under 35 U.S.C. 154(b) by 24 days.

(21) Appl. No.: 10/817,059

(22) Filed: Apr. 2, 2004

Related U.S. Application Data

(62) Division of application No. 10/403,702, filed on Mar. 31, 2003.

(51) Int. Cl.⁷ .............................................. G01N 11/14
(52) U.S. Cl. .................. 73/54.28; 73/54.23; 73/54.26; 73/54.27; 73/54.37; 73/54.38
(58) Field of Search ........................... 73/54.28, 54.27, 73/54.26, 54.23, 54.37, 54.38

(56) References Cited

U.S. PATENT DOCUMENTS

| | | | |
|---|---|---|---|
| 2,484,761 A | * | 10/1949 | Stock ........................ 73/54.33 |
| 3,435,666 A | | 4/1969 | Fann |
| 4,062,225 A | | 12/1977 | Murphy, Jr. et al. |
| 4,077,252 A | * | 3/1978 | Stutz et al. ................ 73/54.33 |
| 4,175,425 A | | 11/1979 | Brookfield |
| 5,535,619 A | | 7/1996 | Brookfield |
| 5,763,766 A | | 6/1998 | Robinson |

* cited by examiner

*Primary Examiner*—Hezron Williams
*Assistant Examiner*—André K. Jackson

(57) ABSTRACT

Viscometer (80) with a sample cup (42) rotatable by a pulley (26) and a timing belt (30) to shear a tested fluid thus imparting torque to a bob (44) mounted on a shaft (10) supported via a frictionless bearing (58), an optical distance sensor assembly (12) measures the distance to an arm (70) which is connected to the top of shaft (10). This distance information is further converted to the viscosity of the tested fluid.

13 Claims, 5 Drawing Sheets

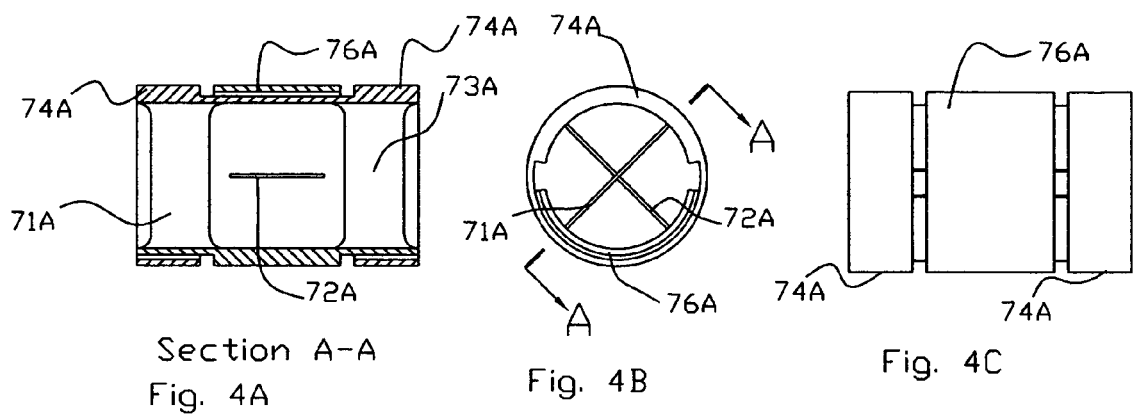
Section A-A
Fig. 4A
Fig. 4B
Fig. 4C
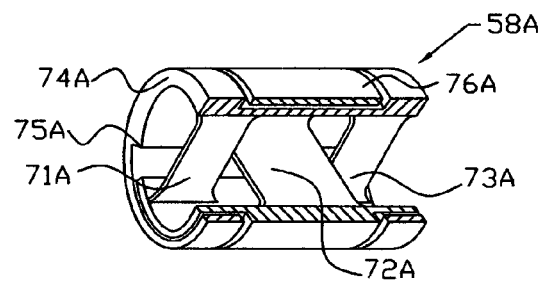
Fig. 4
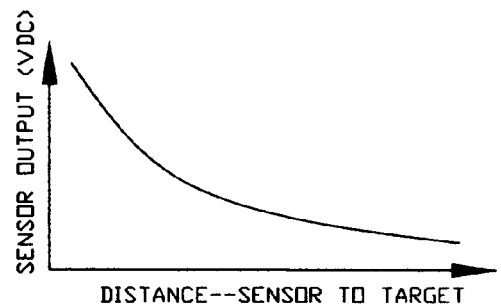
Fig. 5

DIGITAL VISCOMETER WITH FRICTIONLESS BEARING

CROSS-REFERENCE TO RELATED APPLICATIONS

This is a division of Ser. No. 10/403,702, filed Mar. 31, 2003.

BACKGROUND—FIELD OF INVENTION

The present invention relates to measurement of viscosity with a frictionless bearing.

BACKGROUND—DESCRIPTION OF PRIOR ART

A liquid between two surfaces will shear when one surface moves relative to the other. The force needed to make such a movement is directly related to the viscosity of the liquid (with the mechanical configuration factored out). Viscometers typically rotate a bob within a cylinder still with the liquid therebetween, or rotate an outer cylinder while keeping the inside coaxial bob inert. In such examples, torque is directly related to the viscosity of the liquid (again with mechanical configuration factored out).

Several types of arrangement have been applied to measure the torque due to the viscosity of the liquid. In U.S. Pat. No. 3,435,666, a helical spring is attached to the inside bob through a bob shaft while driving the outer cylinder. The shear force applied on the bob is proportional to the torque applied by the liquid, which is also measured by a strain gauge torque transducer. One of the drawbacks of this design is that two bearings are required to mount the bob and bob shaft assembly. Those traditional bearings have drag force, which adds extra error in the reading. Also, those bearings can be corroded easily under high temperature and corrosive sample vapors. Thus, it has been a major task to maintain those bob shaft bearings working properly for this type of viscometers. In U.S. Pat. No. 5,535,619, a torque tube is attached to the inside bob while driving the outer cylinder. The toque applied on the bob causes a rotational deflection on the readout wire, which is inside of a torque tube. The readout wire is in turn mounted on a rigid jewel support located in the instrument head. An electromagnetic sensor pickup the rotations of the readout wire. One of the drawbacks of this design is that the torque tube and readout wire is structurally weak in order to generate detectable amount of deflection for the electromagnetic sensor. Thus excessive load can easily damage it. Another drawback of this design is that the lower end of the torque tube and readout wire is located in hot sample zone. High temperature can change the spring property of the torque tube and readout wire. This is the reason that this type of viscometer has poor accuracy and large zero drift at elevated sample temperatures.

It is an object of this invention to provide a reliable, rugged and temperature stable instrument with integrated electronics usable in viscosity measuring applications, under atmospheric, pressurized, low and high temperature conditions.

It is another object of this invention to provide a viscometer that operates with a wide range of liquids with viscoelasticity property measurement capability.

It is another object of this invention to provide a viscometer that eliminates measurement errors due to conventional bearing frictions.

It is another object of this invention to provide a viscometer that requires substantially less maintenance work yet meets industry standards of accuracy, reliability, durability, dependability, and ease of cleaning.

SUMMARY

A viscometer in accord with the present invention conveniently comprises a stationary frame from which a rotateble sample cup is suspended and includes a means for rotating the sample cup. Suspended within the sample cup is a bob capable of small angular motion about the longitudinal axis of the sample cup. The device is constructed so that the bob and the inside of the sample cup are immersed within the liquid, the viscosity of which is to be determined. The bob is suspended from the stationary frame by a resilient frictionless bearing and a bob shaft. The resilient frictionless bearing permits limited angular motion about its center of rotation. With incremental torque applied on bob, this resilient frictionless bearing will increase its angular deflection before said limit is reached. However the relationship between said torque and said angular deflection does not have to be linear. An arm is attached to the bob shaft or extended portion of the bob, and a non-contact distance sensor measures the movement of the arm. Given the known characteristics of the viscometer, the distance sensor output can be translated to the viscosity of the liquid.

The apparatus and method of the present invention provide a fast response, bi-directional way to measure the shear stress property of fluid under shear condition.

DRAWING FIGURES

Other objects, features and advantages will be apparent from the following detailed description of preferred embodiments taken in conjunction with accompanying drawing in which.

Figures 3A, 3B, 3C:
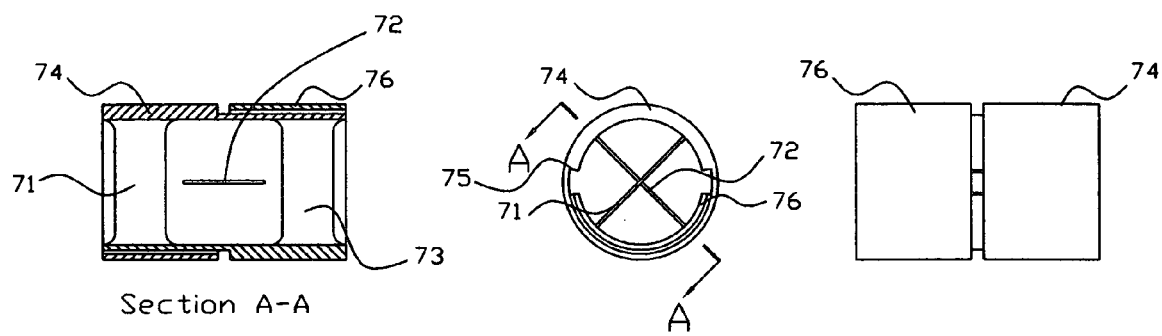
Figure 3:
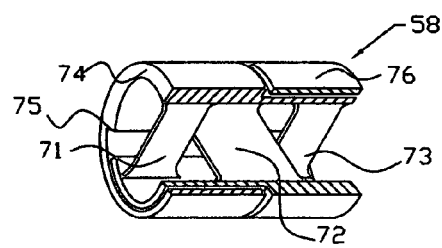
Figure 3D:
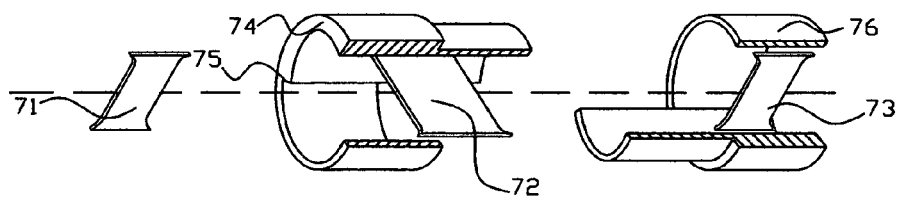
Figures 6, 6A:
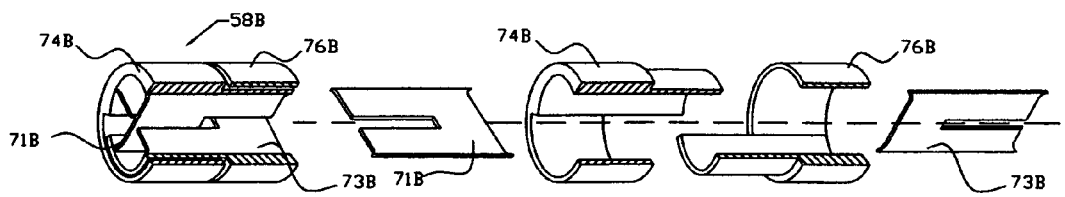
Figures 7, 7A:
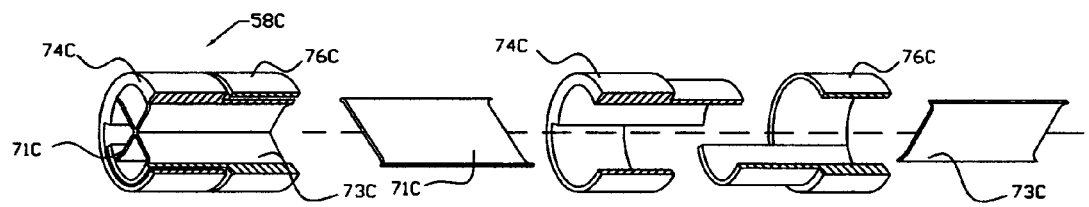
Figures 8, 8A, 9A, 9B:
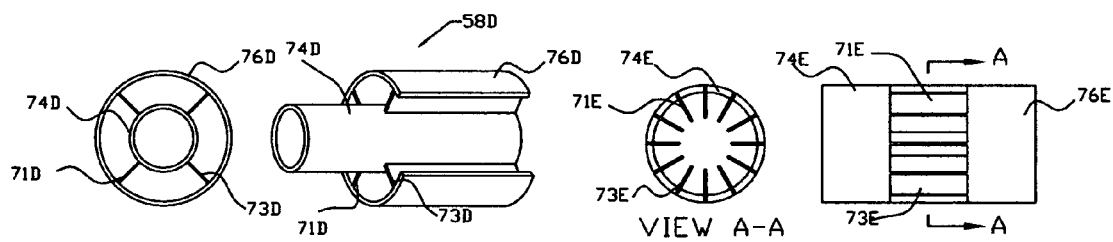
Figure 9:
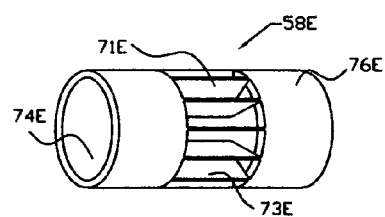

FIG. 3 is an isometric view of a resilient frictionless bearing with two sleeves; FIG. 3A is an end view of the frictionless bearing in FIG. 3; FIG. 3B is a cross-section view of the frictionless bearing in FIG. 3; FIG. 3C is a side view of the frictionless bearing in FIG. 3; FIG. 3D is a dissembled view of the frictionless bearing in FIG. 3;

FIG. 4 is an isometric view of a resilient frictionless bearing with three sleeves; FIG. 4B is an end view of the frictionless bearing in FIG. 4; FIG. 4A is a cross-section view of the frictionless bearing in FIG. 4; FIG. 4C is a side view of the frictionless bearing in FIG. 4;

FIG. 5 is a typical non-contact distance sensor voltage output corresponding to distance;

FIG. 6 is an isometric view of another resilient frictionless bearing with two slotted leaf spring; FIG. 6A is a dissembled view of the frictionless bearing in FIG. 6;

FIG. 7 is an isometric view of another resilient frictionless bearing with two crossed leaf spring; FIG. 7A is a dissembled view of the frictionless bearing in FIG. 7;

FIG. 8 is an isometric view of another resilient frictionless bearing with two different size sleeves; FIG. 8A is an end view of the frictionless bearing in FIG. 8;

FIG. 9 is an isometric view of another frictionless bearing with multiple leaf springs; FIG. 9A is an cross-section view of the frictionless bearing in FIG. 9; FIG. 9B is a side view of the frictionless bearing in FIG. 9.

Reference Numerals in Drawings

| | | | |
|---|---|---|---|
| 10 | bob shaft | 12 | fiberoptic displacement sensor assembly |
| 13 | bath temperature probe | 14 | pressure port |
| 16 | set-in screw | 18 | screw |
| 20 | thermal couple | 22 | snap ring |
| 24 | spacer | 26 | pulley |
| 28 | rotor | 29 | support plate |
| 30 | timing belt | 31 | set-in screw |
| 32A | bearing | 32B | bearing |
| 32C | bearing | 34 | snap ring |
| 36 | o-ring | 38 | dynamic seal retainer |
| 39 | thread | 40 | anti-climber |
| 41 | screw | 42 | sample cup |
| 43 | bath fluid | 44 | bob |
| 45 | thread | 46 | dynamic seal |
| 47 | o-ring | 48 | thread |
| 50 | sample | 52 | cap |
| 56 | main shaft | 58 | frictionless bearing |
| 58A | frictionless bearing | 58B | frictionless bearing |
| 58C | frictionless bearing | 58D | frictionless bearing |
| 58E | frictionless bearing | | |
| 60 | lock nut | 61 | gap |
| 62 | gap | 64 | screw |
| 66 | o-ring | 68 | fitting |
| 70 | arm | 71 | leaf spring |
| 71A | leaf spring | 71B | leaf spring |
| 71C | leaf spring | 71D | leaf spring |
| 71E | leaf spring | 72 | leaf spring |
| 72A | leaf spring | 73 | leaf spring |
| 73A | leaf spring | 73B | leaf spring |
| 73C | leaf spring | 73D | leaf spring |
| 73E | leaf spring | | |
| 74 | stainless steel shell | 74A | stainless steel shell |
| 74B | stainless steel shell | 74C | stainless steel shell |
| 7D | stainless steel shell | 74E | stainless steel shell |
| 75 | stage stop | 75A | stage stop |
| 76 | stainless steel shell | 76A | stainless steel shell |
| 76B | stainless steel shell | 76C | stainless steel shell |
| 76D | stainless steel shell | 76E | stainless steel shell |
| 80 | viscometer | | |

DESCRIPTION—FIGS. 1, 2, 3, 3A, 3B, 3C and 3D—PREFERRED EMBODIMENT

Figure 1:
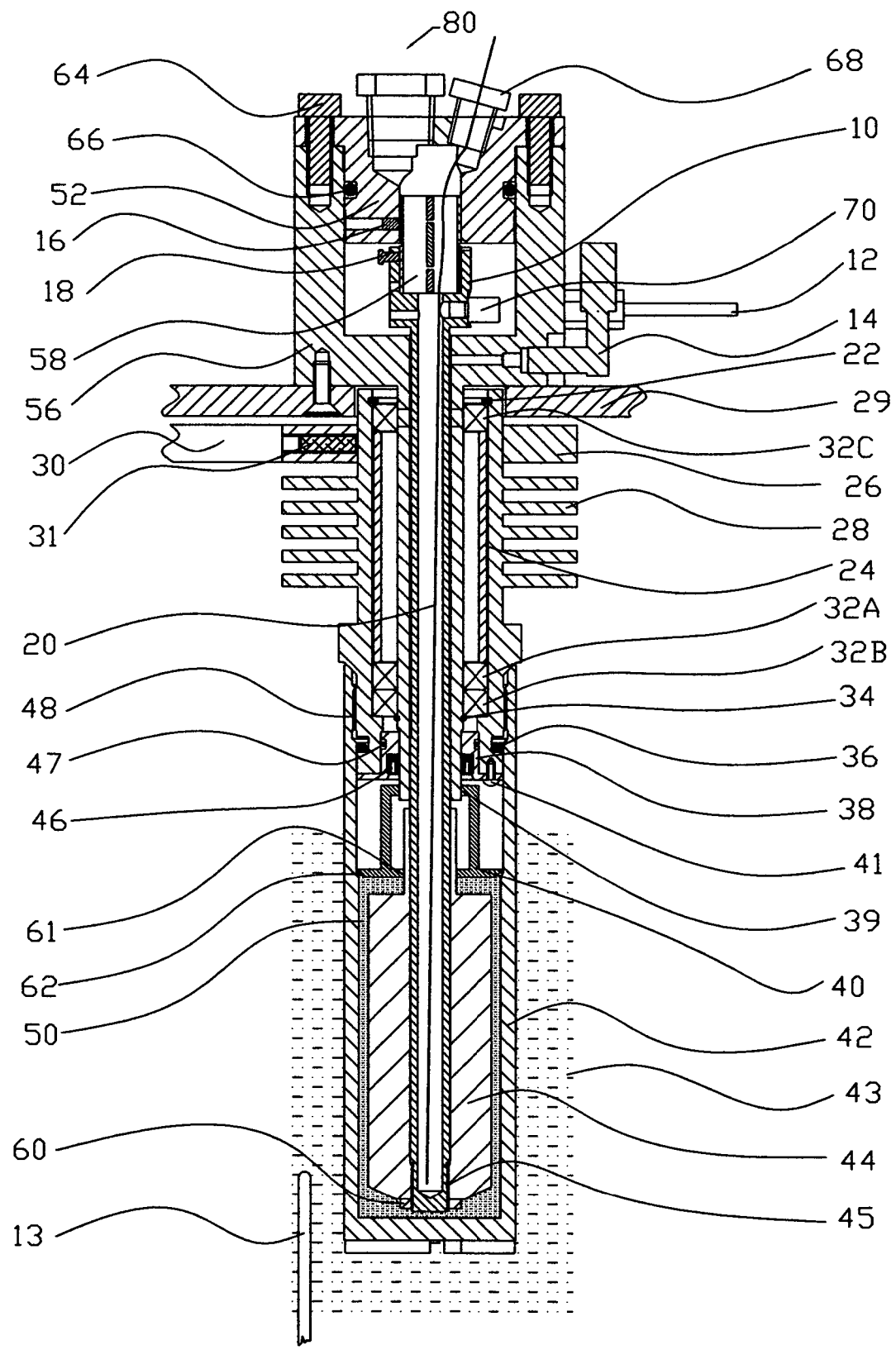
FIG. 1 is a cross-section view of a preferred embodiment of the invention.

FIG. 1 is a cross-section view of a viscometer 80 with a bob 44 and a sample cup 42 with a sample liquid 50. Sample cup 42 is detachable from a rotor 28 via a screw thread 48. An o-ring 36 assures against gas escapes and/or escape of tested fluid through thread 48. Rotor 28 is mounted on a main shaft 56 through axially spaced bearings 32A, 32B, 32C with snap rings 22 and 34. Bearing 32A, 32B and 32C are needed for alignment, and a spacer 24 is to keep bearings 32A, 32B and 32C in places. A sprocket 26 is secured to rotor 28 by a set-in screw 31. A motor-driven timing belt 30 transmits the power to turn sprocket 26. Main shaft 56 and a motor are mounted to a support plate 29.

A cap 52 is tightened down to main shaft 56 with screw 64. An o-ring 66 prevents leakage between cap 52 and main shaft 56. One sleeve of a frictionless bearing 58 is inserted into the inside bore of cap 52, and is secured with a set-in screw 16. The other sleeve of frictionless bearing 58 is secured to a bob shaft 10 with a screw 18. Bob shaft 10 extends from top to the lower portion of sample cup 42. Bob shaft 10 does not have contact with the inside wall of main shaft 56. A bob 44 is coaxially supported from bob shaft 10 by a thread 45. A lock nut 60 is screwed onto the bottom of bob shaft 10.

A dynamic seal retainer 38 is fixed to rotor 28 with a screw 41. A dynamic seal 46 prevents the leakage of gas when there is relative movement between main shaft 56 and dynamic seal retainer 38. An o-ring 47 prevents the leakage of gas between rotor 28 and dynamic seal retainer 38.

An anti-climber 40 is screwed on main shaft 56 through thread 39. Anti-climber 40 bottom edge has a small gap 62 with sample cup 42 inside wall, and there is a small gap 61 between inside wall of anti-climber 40 and outside wall of bob 44. This small gap 61 and 62 can keep sample 50 down at its measurement zone while preventing it climbing up.

A fitting 68 allows a thermal couple 20 going through while preventing the leakage of gas as well. A thermal couple 20 goes to the bottom of bob shaft 10 in order to get an accurate sample temperature reading. Nitrogen or pressurization media is applied through a fitting 14 to pressurize the whole pressure chamber.

Sample cup 42 is dipped into a bath fluid 43. A bath temperature probe 13 measures the temperature of bath fluid 43 in order to control its temperature.

Figure 2:
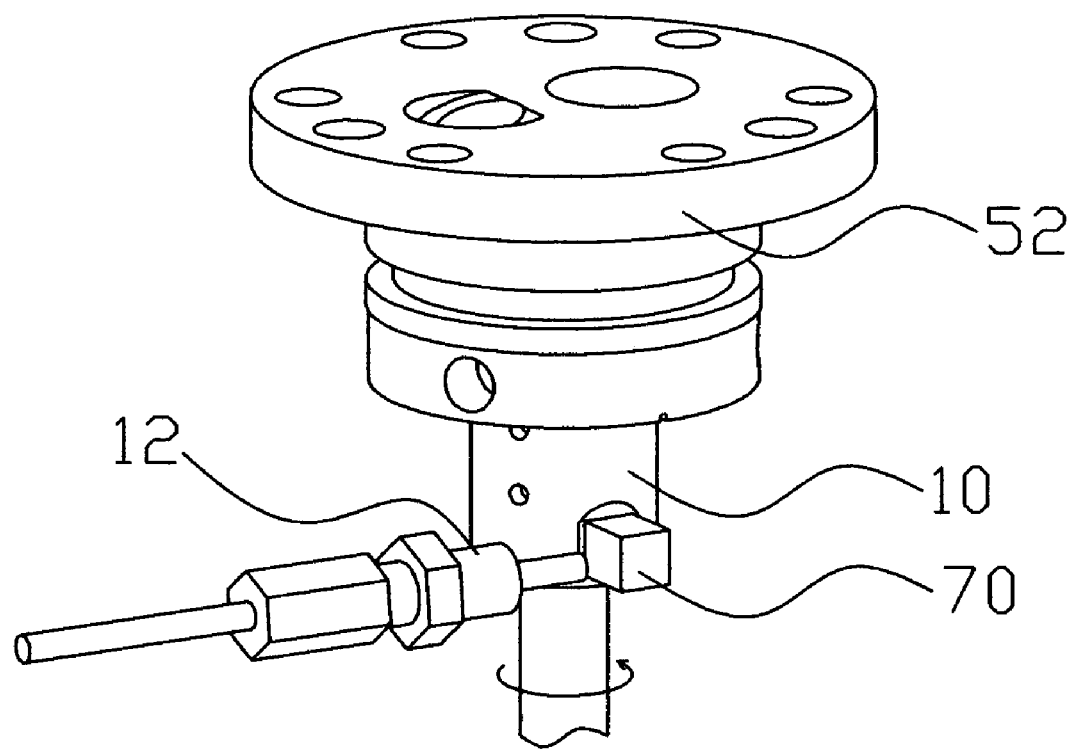
FIG. 2 is an isometric view of the top portion of the preferred embodiment with main shaft 56 hidden for clarity.

FIG. 2 is an isometric view of the top portion of viscometer 80 with main shaft 56 hidden for clarity. In FIG. 2, an arm 70 is screwed onto the side wall of bob shaft 10. A fiberoptic displacement sensor assembly 12 is mounted on the side wall of main shaft 56. Fiberoptic displacement sensor assembly 12 consists of a mounting fitting, a stainless steel tubing shield, a transparent sapphire window in front of the tubing shield and a bare fiberoptic displacement sensor inside of the tubing shield. This fiberoptic displacement sensor assembly 12 is commercially available from Philtec Inc., Arnold, Md. Preferred model is D-63W. The operation theory of a fiberoptic displacement sensor is not in the scope of this invention and is readily available on Philtec Inc. web sites. The stainless steel tubing shield and the Sapphire window of fiberoptic displacement sensor assembly 12 separate the electronic and fragile portions of the sensor from pressurized zone, and prevent possible overload and corrosive damages to them as well.

FIG. 3 shows an isometric view of frictionless bearing 58 with two sleeves. FIG. 3A is an end view of the frictionless bearing in FIG. 3; FIG. 3B is a cross-section view of the frictionless bearing in FIG. 3; FIG. 3C is a side view of the frictionless bearing in FIG. 3; FIG. 3D is a dissembled view of the frictionless bearing in FIG. 3. Frictionless bearing 58 consists of two stainless steel shells 74 and 76 held in position by three leaf springs 71, 72 and 73 on two perpendicular planes. As shown in FIG. 3D, both stainless steel shells 74 and 76 are consisting of an outside-smooth cylindrical portion and a smaller OD arc shell portion. The outside-smooth cylindrical portions of stainless steel shells 74 and 76 are disposed coaxially and have same OD. Each of the smaller arc shell portions of stainless steel shells 74 and 76 is inserted into the outside-smooth cylindrical portion of the other. Leaf springs 71 and 73 are disposed on one common plane while leaf spring 72 is in another. Leaf springs 71, 72 and 73 all have their one end welded to stainless steel shell 74 while the other end welded to stainless steel shell 76. There is no direct contact between stainless steel shells 74 and 76—eliminating friction. Additionally, leaf springs 71, 72 and 73 also provide the pivotal action corresponding to the common axis of stainless steel shells 74 and 76, which is inherently self-centering and requires no lubrication or maintenance. A stage stop 75 stops further relative movement between stainless steel shell 74 and stainless steel shell 76 when excessive torque load is applied on frictionless bearing 58.

OPERATION—FIGS. 1, 2, 3, 3A, 3B, 3C, 3D and 5—PREFERRED EMBODIMENT

During operation, a motor drives sprocket 26 rotating in counter clockwise direction viewing from the top of viscometer 80, through timing belt 30. Rotor 28 and sample cup 42 rotates together with pulley 26. Then a torque is applied to bob 44 due to the viscosity of sample 50. This torque is transferred to frictionless bearing 58 through bob shaft 10. This torque also causes a small counter clockwise direction deflection on frictionless bearing 58 as shown in FIG. 2. Arm 70 rotates with bob shaft 10, hence the distance between fiberoptic displacement sensor assembly 12 and arm 70 increases. The signal of fiberoptic displacement sensor assembly 12 is processed and collected thereafter. FIG. 5 shows dc voltage output vs. distance relationship for a typical fiberoptic distance sensor. As shown in FIG. 5, when distance is small, the slope of the curve is steep. Thus small distance change can cause large voltage output change. This ensures viscometer 80 has good resolution and accuracy when fluid shear stress applied on bob 44 is low. Meanwhile, when distance becomes larger, the slope of the curve becomes more leveled. Thus large distance can still be measured. This ensures viscometer 80 possesses wide measurement range.

Before operation, viscometer 80 need be calibrated. A series of different shear stress vs. sensor voltage output data are collected and a polynomial curve fitting is performed. Thus the non-linearity of sensor voltage output vs. shear stress is not a problem.

Additionally, frictionless bearing 58 is located on top where temperature is relatively low and constant. Therefore, elevated sample temperature does not affect the property of frictionless bearing 58. This ensures the temperature stability of viscometer 80.

Furthermore, there is an initial small gap between arm 70 and the tip of fiberoptic displacement sensor assembly 12 when fluid shear stress applied on bob 44 is zero. When sample cup 42 is driven to rotate in clockwise direction viewing from the top of viscometer 80, the distance between fiberoptic displacement sensor assembly 12 and arm 70 decreases. Therefor as long as fiberoptic displacement sensor assembly 12 and arm 70 do not contact, viscometer 80 can measure fluid shear stress applied on bob 44 no matter sample cup is rotating in clockwise or counter clockwise directions. So, this invention can measure visco-elasticity property of fluids when sample cup 42 is under dynamic vibrating movement.

Ramifications

There are many other ways to hold two sleeves together with two leaf springs. For example, FIGS. 6, 6A, 7 and 7A show 2 other possible ways to hold two sleeves together with two leaf springs.

FIGS. 8 and 8A demonstrate that frictionless bearing 58D can have two different outside diameter sleeves as well.

Frictionless bearing 58E can have more than 2 leaf springs as well, which is clearly shown in FIGS. 9, 9A and 9B.

In preferred embodiment viscometer 80, frictionless bearing 58 can have more than 2 outside sleeves. For example, in FIGS. 4, 4A, 4B and 4C frictionless bearing 58A has 3 sleeves looking from outside. The two end sleeves are actually one sleeve 74A. In this case either one of shell 74A or 76A can be directly or in-directly mounted on cap 52, and the other one will rotate together with bob 44.

The sleeves of frictionless bearing 58, 58A, 58B, 58C, 58D and 58E do not have to be round shape, they could be square or other shapes.

Frictionless bearing 58, 58A, 58B, 58C, 58D and 58E can be made of Hastlloy, titanium or other exotic material in stead of stainless steel, in order to enhance its linearity, corrosion resistance, overall strength, etc.

There are many other ways to measure the angular displacement of bob shaft 10. For example, in preferred embodiment viscometer 80, arm 70 and fiberoptic displacement sensor assembly 12 can be replaced with a pair of concentrically mounted electrical stator and rotor to measure the rotation of bob shaft 10.

In preferred embodiment viscometer 80, arm 70 and fiberoptic displacement sensor assembly 12 can be replaced with an encoder to measure the rotation of bob shaft 10.

Alternatively, a metal arm or wiper which rotates with bob shaft 10, and a wire-wound conductance transducer which is mounted directly or indirectly on cap 52 or main shaft 56, can also be used to measure the rotation of bob shaft 10 by measuring the conductance change in the wire-wound coil.

In preferred embodiment viscometer 80, fiberoptic displacement sensor assembly 12 can be replaced with any other kinds of non-contact sensors, which can sense the distance change of targets, such as eddy current effect sensors, hall effect sensors, magnetic field sensors, etc. Eddy current effect sensors and magnetic field sensors also possess similar voltage output vs. distance correlation as shown in FIG. 5.

Viscometer 80 can also be reduced to much simpler construction for non-pressurized viscometer applications. It can be accomplished by removing sealing related components, such as all o-rings, dynamic seal retainers, etc. In non-pressurized application, sample cups can have open bottoms, and the lower part of sample cups can be immersed into a liquid—the liquid's viscosity to be measured.

Conclusion, and Scope

Accordingly, the reader will see that this invention can be used to construct a durable and economic electronic viscometer easily. The fast response and bi-directional measurement capability of this invention also makes sophisticated transient measurement of liquid property easy.

Objects and Advantages

From the description above, a number of advantages of my viscometer become evident:

(a) Due to elimination of traditional bob shaft bearings, current invention substantially reduces maintenance task.

(b) Totally eliminate the measurement error because of bearing drag in a traditional viscometer.

(c) Elevated sample temperature does not affect the measurement accuracy, because frictionless bearing and non-contact distance sensor are located on top where temperature is relatively low and constant.

(d) Very conveniently isolate the electronic portion of sensors from possible contamination or corrosion by sample.

(e) Due to the exponential output natural of most non-contact distance sensor, current invention covers very wide measurement range while maintaining excellent sensitivity and accuracy when measurement values are low.

(f) Very robust structure can handle extremely overload. Because sensor in this invention does not directly contact any moving parts, overload capacity is not limited by the load capacity of the sensor.

(g) If high sensitive non-contact sensor is selected in current invention, torque induced rotational deflection can be designed very small. So the momentum of torsion assembly can be very small. Thus the response time of torque change can be very little.

(h) When non-contact sensors are used to measure bi-directional movement of arm, this invention can measure visco-elasticity of fluid under dynamic vibrating movement.

Further objects and advantages of my invention will become apparent from a consideration of the drawings and ensuing description.

I claim:

1. Viscometer instrument comprising:
   (a) a rotor which is driven to rotate while contacting with a sample liquid to be measured,
   (b) means for driving said rotor to rotate,
   (c) a bob within said rotor,
   (d) means for directly or indirectly sensing the rotation of said bob,
   (e) means for suspending said bob comprising:
      (1) at least two axially disposed sleeves that do not directly contact with each other, and said sleeves are arranged so that at least one of said sleeves is mounted on a stationary frame, and at least one of the other sleeves directly or indirectly connecting to a portion of said bob, and moves together with said bob,
      (2) one or more leaf springs that hold said sleeves together, and at least some of said leaf springs have their two ends connected to two different said sleeves.

2. The instrument of claim 1 wherein said axially disposed sleeves are coaxial.

3. The instrument of claim 2 wherein said two coaxial sleeves are cylindrical.

4. The instrument of claim 3 wherein said two coaxial sleeves have same outside diameter.

5. The instrument of claim 3 wherein said two coaxial sleeves have different outside diameter.

6. The instrument of claim 3 wherein said two coaxial sleeves have angular displacement relative to each other when a torque is applied on said bob.

7. The instrument of claim 6 wherein said angular displacement is approximately linear corresponding to said torque that applied on said bob.

8. The instrument of claim 1 wherein a bob shaft is used to connect said bob to said means for suspending said bob.

9. The instrument of claim 1 wherein said means for suspending said bob is mounted away from said sample liquid so that temperature effects and corrosion damage are minimized.

10. The instrument of claim 1 wherein said means for sensing the rotation of said bob is a pair of concentrically mounted electrical stator and rotor.

11. The instrument of claim 1 wherein said means for sensing the rotation of said bob is a strain gauge.

12. The instrument of claim 1 wherein said means for sensing the rotation of said bob is a metal arm and a wire wound conductance sensor.

13. The instrument of claim 1 wherein said means for sensing the rotation of said bob consists of, a member rotating with said bob and a sensor measuring the distance to the said member while not contacting it.

* * * * *